United States Patent [19]

Rabin et al.

[11] Patent Number: 5,057,412

[45] Date of Patent: * Oct. 15, 1991

[54] ENZYMIC METHOD OF DETECTING ANALYTES AND NOVEL SUBSTRATES THEREFOR

[75] Inventors: Brian R. Rabin, Potters Bar; Michael R. Hollaway, East Molesey; Christopher J. Taylorson, Chiswick, all of England

[73] Assignee: London Biotechnology Limited, London, England

[*] Notice: The portion of the term of this patent subsequent to May 17, 2005 has been disclaimed.

[21] Appl. No.: 167,756

[22] Filed: Mar. 15, 1988

Related U.S. Application Data

[62] Division of Ser. No. 715,236, Mar. 22, 1985, Pat. No. 4,745,054.

[30] Foreign Application Priority Data

Mar. 26, 1984 [GB] United Kingdom ................. 8407736

[51] Int. Cl.$^5$ .................... C12Q 1/68; G01N 33/535
[52] U.S. Cl. ........................................ 435/6; 435/4; 435/7.91; 435/18; 435/19; 435/810; 435/966; 435/975; 436/501

[58] Field of Search ...................... 435/4, 6, 7, 18, 19, 435/810, 7.91, 966, 975; 436/501

[56] References Cited

U.S. PATENT DOCUMENTS

| | | | |
|---|---|---|---|
| 4,463,090 | 7/1984 | Harris | 435/7 |
| 4,598,042 | 7/1986 | Self | 435/810 |
| 4,745,054 | 5/1988 | Rabin et al. | 435/6 |

*Primary Examiner*—David A. Saunders
*Attorney, Agent, or Firm*—Oblon, Spivak, McClelland, Maier & Neustadt

[57] ABSTRACT

A small enzymically inactive peptide fragment of an enzyme (e.g. ribonuclease S-peptide) is used as the label and conjugated with the complementary fragment (S-protein) to form an enzyme which catalyses a primary reaction whose product is, or leads to, an essential coenzyme or prosthetic group for a second enzyme which catalyses a secondary reaction leading to a detectable result indicating the presence of analyte. Also disclosed are novel synthetic substrates for the primary reaction. Substrates for ribonuclease S conjugate enzyme are of the formula R-X where R is pyrimidine 3'-phosphate moiety and X is a leaving group linked to R through the 3'-phosphate group and leads to said coenzyme or prosthetic group, e.g. via riboflavin, thiamine, pyridoxal, pyridoxine or pyridoxine phosphate.

9 Claims, 4 Drawing Sheets

ENZYMIC METHOD OF DETECTING ANALYTES AND NOVEL SUBSTRATES THEREFOR

This application is a division of U.S. application Ser. No. 715,236 filed Mar. 22, 1985 now U.S. Pat. No. 4,745,054, issued May 17, 1988.

This invention relates to methods for detecting analytes in sample media by means of enzymic reactions. It is particularly, but not exclusively, applicable to the detection of polynucleotide analytes.

Nucleic acid hybridisation assays are of increasing practical importance for the diagnosis of, and the detection of carriers of, human inherited diseases (for example, see Banbury Report 14, Recombinant DNA Applications to Human Diseases, ed. S. T. Caskey & R. L. White, Cold Spring Harbor Laboratory, 1983). They are valuable also for the identification of pathogenic organisms, including viruses and bacteria, and for identification of genes conferring resistance to antibiotics in the latter.

Commonly used procedures involve the use of radiochemically-labelled probes with the attendant problems of safety, cost and limited shelf-life. Alternative methods of detection have been proposed in which a chemiluminescent, fluorescent or phosphorescent material is attached to the probe (EP 70687), but it is doubtful whether such methods have the sensitivity required to detect the presence of the $10^{-18}$ moles of a single copy gene typically available for determination.

Another approach has been to attach the probe to biotin and use avidin coupled to a suitable enzyme for the purpose of detection (GB 2019408). The sensitivity of this method is limited by the number of molecules of the detector enzyme that can be attached to avidin.

EP 27036 proposes an assay system using a conjugate between a probe and an enzyme, the enzyme then taking part in a primary reaction which produces or removes a "modulator" for a secondary reaction system; the modulator being a substance which gives rise to a catalytic event in the secondary reaction system, but of which there is no net consumption during the catalytic event. This therefore gives rise to an amplification factor between the primary and secondary reaction systems. The modulator may be an enzyme activator or inhibitor, or a cyclicly regeneratable substrate for the secondary system.

Assay systems using secondary reactions to achieve amplification are likewise disclosed in WO 81/00725, which refers to the use of cyclising substrates, and in EP 49606, which refers to the primary reaction producing a "facilitator" which enhances the rate of the secondary reaction.

In enzyme-linked immunoassay systems it is usual for the labelling enzyme to be conjugated to the probe, and this means that excess enzyme has to be removed very efficiently before the enzyme-catalysed reaction takes place, otherwise a false positive result is obtained. This gives rise to considerable problems, and a high signal/noise ratio is difficult to obtain.

EP 62277 discloses the use of an enzyme based on ribonuclease A. Ribonuclease A can be split into a 20 residue polypeptide, called the S-peptide, and a 104 residue polypeptide, call the S-protein. Neither the S-peptide nor the S-protein alone has enzymic activity, but they will form a conjugate, called ribonuclease S, which has ribonuclease activity. The proposal in the above disclosure is to label an analog of the analyte with the S-peptide, so that the assay medium contains labelled analog and unlabelled analyte. An antibody is then introduced which can attach itself either to the analyte molecules or to the analog molecules. The analyte thus competes with the analog for binding antibody, and S-peptide on unbound analog molecules are then free to combine with added S-protein and produce enzymic activity. By adding increasing concentrations of the analyte, a displacement curve is constructed which relates catalytic activity to analyte concentration, and it is proposed that this reference curve be used to determine unknown analyte concentrations. The ribonuclease S activity is typically carried out using spectrophotometric or fluorometric techniques. This method of using the S-peptide/S-protein combination appears complicated and difficult, and in principle the determination of analyte by measuring differences in reaction rate would appear to impose limitations on sensitivity, accuracy and ease of execution.

One aspect of the present invention provides a method of detecting an analyte in a sample medium, involving the use of an assay component carrying an enzymically inactive small fraction of a primary enzyme, and the addition of a complementary enzymically inactive protein fraction of the enzyme so as to conjugate to said small fraction and produce an active primary enzyme, and the performance of a reaction catalysed by said enzyme, leading to a detectable result; characterized in that said assay component is a specific recognition probe which binds to the analyte, and said primary enzyme catalyses a reaction which converts a substrate into a primary product which itself, or as a subsequent product produced by a further reaction or series of reactions initiated by said primary product, is a component essential for the catalytic activity of a second enzyme which is thereby completed and catalyses a reaction leading to a detectable result.

Said small fraction of the primary enzyme is preferably a minor peptide fraction of the total enzyme protein. Such a small peptide fraction can be inert to the binding conditions, whereas a complete enzyme could have its activity seriously affected by the conditions, such as extremes of temperature, pH, salt concentration, etc. Suitably it is a ribonuclease S-peptide, and the complementary fraction is the ribonuclease S-protein. The resulting ribonuclease S enzyme then suitably catalyses the conversion of a synthetic substrate to said primary product. The synthetic substrate is suitably a pyrimidine 3'-phosphodiester compound of the formula R—X, where R is a pyrimidine 3'-phosphate moiety and X is a leaving group which forms said primary product, X being liked to R' through the 3'-phosphate group. R can therefore be represented as Cp or Up, where C=cytidine, U=uridine and p=phosphate, or pyrimidine analogs thereof, and optionally substituted, e.g. with a 5'-hydroxy protecting group.

An advantage of the present invention over the prior proposals is that it provides a simple and direct method of enzymically detecting the analyte, with high sensitivity resulting from the secondary amplification, and high signal to noise ratio resulting from the fact that neither of the enzyme fractions (e.g. S-peptide and S-protein) have enzymic activity which can give rise to background "noise", so that the specific enzymic activity only arises from conjugate catalyst produced by bound S-peptide, and there is no need to remove excess of the larger enzyme protein fraction.

Synthetic substrate compounds such as R—X (which may be referred to as "prosthetogens") are thought to be novel per se. Therefore another aspect of the present invention provides a synthetic prosthetogen compound which is cleavable by an enzyme to produce a component essential for the catalytic activity of another enzyme, or a precursor therefor. Preferably, the prosthetogen is a pyrimidine 3'-phosphodiester compound of the formula R—X, where R is a pyrimidine 3'-phosphate and X is a leaving group linked to R through the 3'-phosphate group, and enzymically cleavable therefrom to produce an essential component of another enzyme, or precursor therefor.

Another aspect of the invention is an enzyme linked immunoassay procedure in which a primary enzyme whose concentration is related to the presence of analyte to be detected catalyses a primary enzymic reaction leading to a detectable product; characterized in that a substrate for the primary enzyme is a synthetic compound which is cleaved by the primary enzyme to produce directly, or by one or more further reactions, a component essential for the catalytic activity of another enzyme, which is thereby activated to catalyse a secondary enzymic reaction leading to a detectable result.

The present invention thus employs the principle of an enzyme-linked detection system, but an enhancement in the sensitivity of many orders of magnitude is obtained by using the primary catalyst to generate, directly or indirectly, a coenzyme or prosthetic group that is part of another and different catalytic centre employing an enzyme which depends absolutely on said coenzyme or prosthetic group for catalytic activity. The primary enzymic reaction can therefore produce a coenzyme or prosthetic group directly, or it can produce a precursor which is then converted, e.g. enzymically, to the coenzyme or prosthetic group. The coenzyme or prosthetic group, whether produced directly or indirectly, is then combined with a suitable apoenzyme to produce a holoenzyme, the quantity of which can be assayed by using the holoenzyme to catalyse a secondary reaction system leading to a detectable result, such as the formation of a dye.

A preferred assay procedure is shown in Scheme 1 below.

All catalysts are boxed and placed above an arrow indicating the reaction catalysed. The primary enzyme is $E_o$ and the detecting active holoenzyme $E_{2a}X'$.

The probe is attached to a component $A_1$ in a manner so as not to interfere with hybridisation, preferably at either of the free ends of the probe, by a suitable spacer group using, for example, the methodology described in Nucleic Acid Research, Vol. 11 (1983) pp. 659–669. Following hybridisation under appropriate stringency conditions, addition of $A_2$ gives an enzymically active species, $A_1A_2$, designated $E_o$ in Scheme 1, attached to the probe. This is the Recognition Phase of the invention. This primary enzyme, $E_o$, acts catalytically whilst immobilised to the target DNA on a prosthetogen substrate R—X to release the coenzyme or prosthetic group precursor X—OH which, in turn, following conversion where necessary to the active form of the coenzyme $X'$ in a process catalysed by the enzyme $E_1$, combines with an inactive apoenzyme $E_{2i}$ to give the enzymically active detecting holoenzyme $E_{2a}X'$. In some cases the $E_o$-catalysed reaction will produce a coenzyme or prosthetic group directly, in which case the conversion step using enzyme $E_1$ is omitted. The enhancement in sensitivity arises from the fact that, in principle, every molecule of $X'$ produced can give rise to an active molecule of $E_{2a}X'$, and that the number of molecules of $E_{2a}X'$ produced will exceed greatly that of $E_o$ attached to the probe. In this invention $X'$ is part of the catalytic centre of enzyme $E_{2a}X'$ and is not an allosteric activator of the substrate. It is absolutely required for catalytic activity, and is not a mere rate enhancer for an existing enzymic reaction, as is the case with some of the prior art proposals. Enzyme $E_{2a}X'$ catalyses the formation of an easily detected product P from a substrate S.

An example of the invention employs as the $A_1$ and $A_2$ fragments, S-peptide (Spep) and S-protein (Spr), respectively, derived from bovine pancreatic ribonuclease (EC 3.1.27.5) by proteolytic cleavage with subtilisin (EC 3.4.21.14). It is well known that the enzymically inactive S-peptide and S-protein can combine with very high affinity to generate ribonuclease S which has full ribonuclease A enzymic activity.

The active hybridised probe-$A_1$-$A_2$ complex (hybridised probe-enzyme $E_o$) acts on the prosthetogen substrate R—X which, for example, has the form CpX or UpX where X would be linked through a 3'-phosphodiester linkage (p) to cytidine (C) or uridine (U) nucleoside. The "leaving group" X—OH is a prosthetic group or coenzyme precursor, such as thiamine, riboflavin, pyridoxal or pyridoxine.

It is well known that bovine pancreatic ribonuclease A catalyses the following reactions:

CpX→cytidine 2',3'-cyclic phosphate+X—OH

UpX→uridine 2',3'-cyclic phosphate+X—OH where, although X—OH must be a primary alcohol, there are few other restrictions on its structure in order to act as a suitable leaving group in the ribonuclease-catalysed reaction. (For a review see F. R. Richards and H. W. Wyckoff, in "The Enzymes", Vol. 3, 3rd Edition, 1971, ed. P. D. Boyer, pp. 647-806)

Some examples of the nature of the various components that may be employed in Scheme are given in Table 1.

TABLE 1

| X-OH | $E_1$ | X' |
| --- | --- | --- |
| Riboflavin | Riboflavin kinase (EC 2.7.1.26) | Flavin mononucleotide (FMN) |
| Riboflavin | Riboflavin kinase (EC 2.7.1.26) + FMN Adenyl transferase (EC 2.7.7.2) | Flavin adenine dinucleotide (FAD) |
| Thiamine | Thiamine pyrophosphokinase (EC 2.7.6.2) | Thiamine diphosphate |
| Pyridoxal | Pyridoxal kinase (EC 2.7.1.35) | Pyridoxal 5-phosphate |
| Pyridoxine | Pyridoxine 4-dehydrogenase (EC 1.1.1.65) + Pyridoxal kinase (EC 2.7.1.35) | Pyridoxal 5-phosphate |
| Pyridoxine phosphate | Pyridoxine 4-dehydrogenase (EC 1.1.1.65) | Pyridoxal 5-phosphate |

Suitable apoenzymes to produce enzyme $E_{2a}X'$ from X' will be obvious to workers skilled in the art, as will systems for the detection of P by colour production, fluorescence or luminescence (see, for example, H. Harris and D. A. Hopkinson, Handbook of Enzyme Electrophoresis in Human Genetics, 1976, North-Holland Publishing Co.).

The invention can be further understood from the following more detailed description, which is given by way of example, and should not be regarded as limiting the scope of the invention.

A—THE PROBES

Oligonucleotide probes with the required base sequences for hybridising with polynucleotide analytes can be synthesised by the solid phase, phosphotriester method on a keiselguhr-polydimethylacrylamide support, as described in detail by Gait et al [M. J. Gait et al 1982].

The detection system can also be applied in procedures other than those involving gene probes. Thus, in principle, any antigen-antibody interaction could be monitored with greater sensitivity than current non-radioactive methods, using the present invention.

B—SYNTHESIS OF PROBE-S-PEPTIDE DERIVATIVES

Conventional and routine procedures can be used for linking S-peptide to probe molecules. Such procedures are discussed in EP 62277. Likewise that disclosure refers to the use of modifications to, or analogs of, the Spep-Spr subtilisin cleavage products of ribonuclease A, and also to other cleavable enzymes. The present invention similarly comprehends such variants.

Methods for preparation of RNase S and the separation into S-peptide and S-protein have been described by Doscher(1969) and Chavers & Scheraga (1980) respectively.

Reaction of the bifunctional reagent SPDP (n-succinimidyl 3-(2-pyridyldithio)propionate) with the S-peptide gives a derivative containing one mole of reagent per mole of peptide. Substitution at the α-amino group of the N-terminal lysine is a preferred position, as this residue does not contribute significantly to the S-peptide - S-protein interaction.

This derivative, I, is reactive towards thiol reagents and so can be employed to couple an oligonucleotide that has been "G-tailed" by the method of Roychoudhury et al (1976) and reacted with N-acetyl-N'-(p-glyoxylbenzoyl)cysteamine according to the methods of Cheng et al (1983). The reaction scheme is as follows.

The use of compound II to detect the presence of DNA containing sequences complementary to those in the probe can be represented as follows.

where the zig-zig lines represent the complementary sequences of the probe and target sequences in the DNA.

Reaction (ii) can be regarded as optional but may offer advantages in that the S-peptide fragment bears only the relatively small β-mercaptopropionyl group, which would be less likely to diminish enzymic activity than the large probe-DNA complex. This step offers the additional advantage that the S-protein - S-peptide complex would be freed from the matrix to which the DNA has been immobilised.

C—ENZYMIC DETECTION SYSTEMS FOR THE PROBE-S-PEPTIDE DERIVATIVE

A detection system giving a coloured solution or spot on a supporting matrix is preferred as this will simplify and so widen the application of the technology. Greater sensitivity, however, can be achieved by the use of specialised instruments such as luminescence monitors, fluorometers or spectrophotometers.

A general reaction sequence for the system is as follows:

wherein:
P-Spep: probe-S-peptide derivative.
Spr: the S-protein derived from RNase.
$S_1C_1$: a phosphodiester substrate for RNase containing the coenzyme or coenzyme precursor $C_1'$ as the leaving group.
Modifying enzymes: active enzymes which generate the form of the coenzyme required for combination with Apo 1.
Apo 1: the enzymically inactive apoenzyme for which $C_1$ is the coenzyme.
Holo 1: the active holoenzyme formed by combination of Apo 1 with the coenzyme $C_1$.
$S_2$: the substrate for Holo 1 which gives the coloured product P*.
Enzymically active components are shown as enclosed in rectangles with dotted arrows pointing towards the reactions catalysed.

The S-peptide: S-protein interaction

The system exploits the tight and specific binding of the S-peptide to the S-protein. This interaction is of such high affinity that it has not proved possible to determine a value for the dissociation constant ($K_{diss}$), but an upper limit of $K_{diss}$ has been put at $5 \times 10^{-9}$ M by Richards & Vithayathil (1959 a,b). Thus with a concentration of S-protein catalyst of $10^{-7}$ M or less, 95% of the probe would be converted to primary catalyst. RNase S exhibits enzymic activities that are very similar to those of the native RNase A [Takahashi et al (1969)].

In the following presentation specific proposals are made for the nature of the coupling coenzyme, $C_1$, and final detection system ($S_2 \rightarrow P^*$). However there is a large number of alternative possible processes based on other coupling coenzymes and other visualisation procedures.

The detection system with riboflavin as the coupling coenzyme

In this case the substrate for enzymic action by the probe-S-peptide - S-protein complex would be of the following type (III).

where C=cytosine (or other pyrimidine base).

Synthesis of substrate III (Cp Riboflavin)

The substrate Cp riboflavin can be prepared by taking advantage of the reversibility of the first step of ribonuclease A action to synthesise a substrate III consisting of cytidine linked via a 3' phosphate moiety to the terminal hydroxyl residue of the ribityl side chain of riboflavin.

R = Riboflavin

Because of the high hydrolytic activity of RNase A, only small yields of substrate would be expected if the reaction were carried out in aqueous solution. Therefore the reaction was carried out in 50% formamide at −20° C., with the highest possible concentration of riboflavin as the attacking group, with the requisite primary alcoholic group as the nucleophile.

Experimental

I. Enzyme catalysed production of Cp Riboflavin

The reaction was performed at −20° C. with 600 mg of cytidine 2',3'-cyclic phosphate, 1 g of riboflavin and 1 mg/ml ribonuclease A in a total volume of 1130 mls of 50% v/v formamide/buffer pH 6.50.

(The reaction mixture must be maintained away from the light and on the acid side of neutrality to avoid the breakdown of riboflavin to lumiflavin.)

Figure 1:
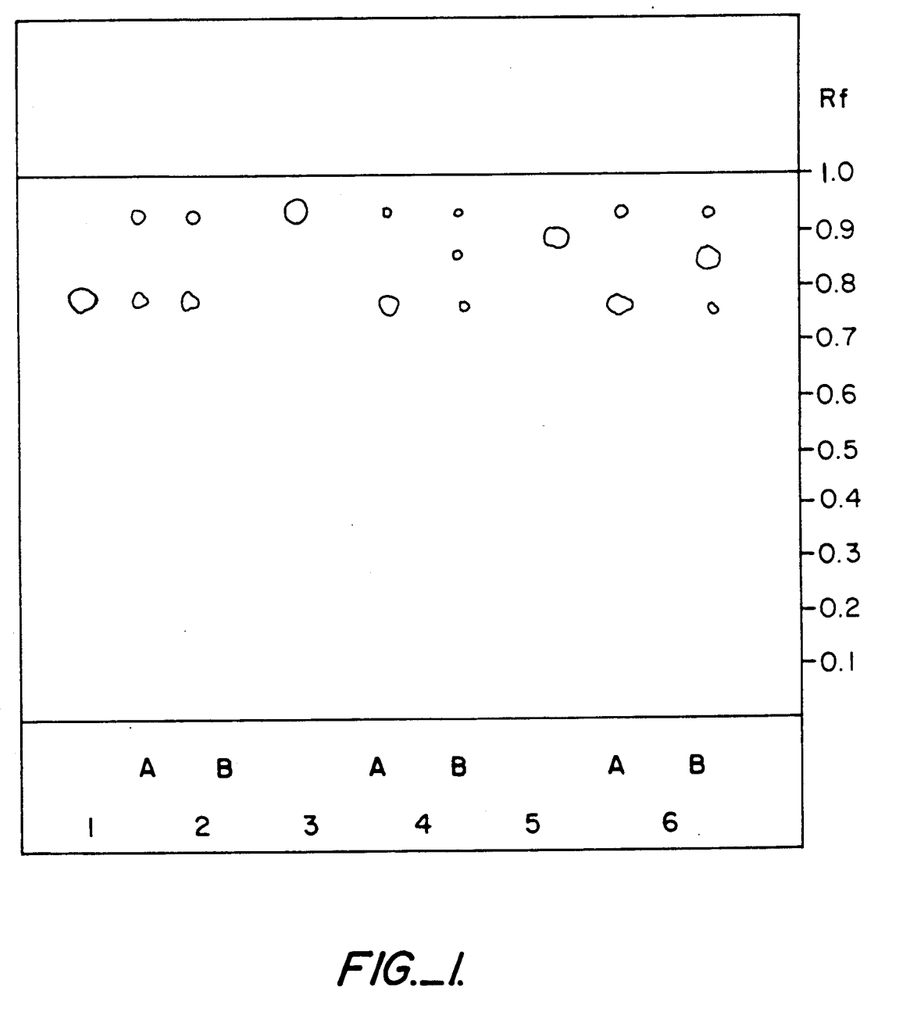
FIG. 1 shows a silica gel chromatogram indicating the course of the reaction for the production of Cp riboflavin. The gel is visualized under UV light at 284 nm and 360 nm, and the lanes on the gel are as follows:
1. Riboflavin (5 ug).
2. (A). Control incubation (no RNAse) time point 0.
2. (B). Incubation (+RNAse), time point 0.
3. Cytidine 2',3'-cyclic phosphate (5 ug).
4. (A). Control incubation, 11 days. (B) Incubation (+RNAse), 11 days.
5. CpA (cytidine adenosine phosphodiester) (5 ug).
(6). Control incubation, 31 days. (B). Incubation (+RNAse), 31 days.

Progress of the reaction was monitored by using thin layer chromatography. Aliquots (100 μl), were withdrawn at regular intervals (5 days) and chromatographed on Whatman PLK Sf silica gel plates against standards, (5 μg), of riboflavin, cytidine 2',3'-cyclic phosphate and cytidine adenosine phosphodiester (CpA). (FIG. 1)

The solvent used was H$_2$O, 40: pyridine, 10: glacial acetic acid, 1; pH 5.8.

Product began to appear on the chromatographs after 11 days of incubation as a spot with an Rf value of 0.87 compared to the Rf values of 0.79 for riboflavin, 0.95 for cytidine 2',3'-cyclic phosphate and 0.89 for CpA. The reaction was stopped after 31 days when the predominant spot on chromatographs was that at Rf 0.87.

II. Stopping the reaction

It was essential at this point to inactivate the ribonuclease in the incubation mixture as exposure of the product to the enzyme in an aqueous environment would result in its breakdown to cytidine 3'-phosphate and riboflavin.

Therefore, ribonuclease was removed by phenol extraction of the incubate at pH 5.40.

The incubate was extracted with phenol three times and the combined aqueous phases were extracted once with chloroform. This procedure had the added advantage in that it facilitated the removal of a large percentage of the foramide present in the reaction mixture.

The combined aqueous phases were reduced in volume by rotary evaporation at 55° C. prior to separation of product from unreacted riboflavin and cytidine 2',3'-cyclic phosphate on columns of silica gel.

III. Separation of product from unreacted constituents (flash chromatography)

The separation of product from unreacted riboflavin and cytidine 2',3'-cyclic phosphate was effected using intermediate pressure chromatography (Still et al, 1978).

Figure 2:
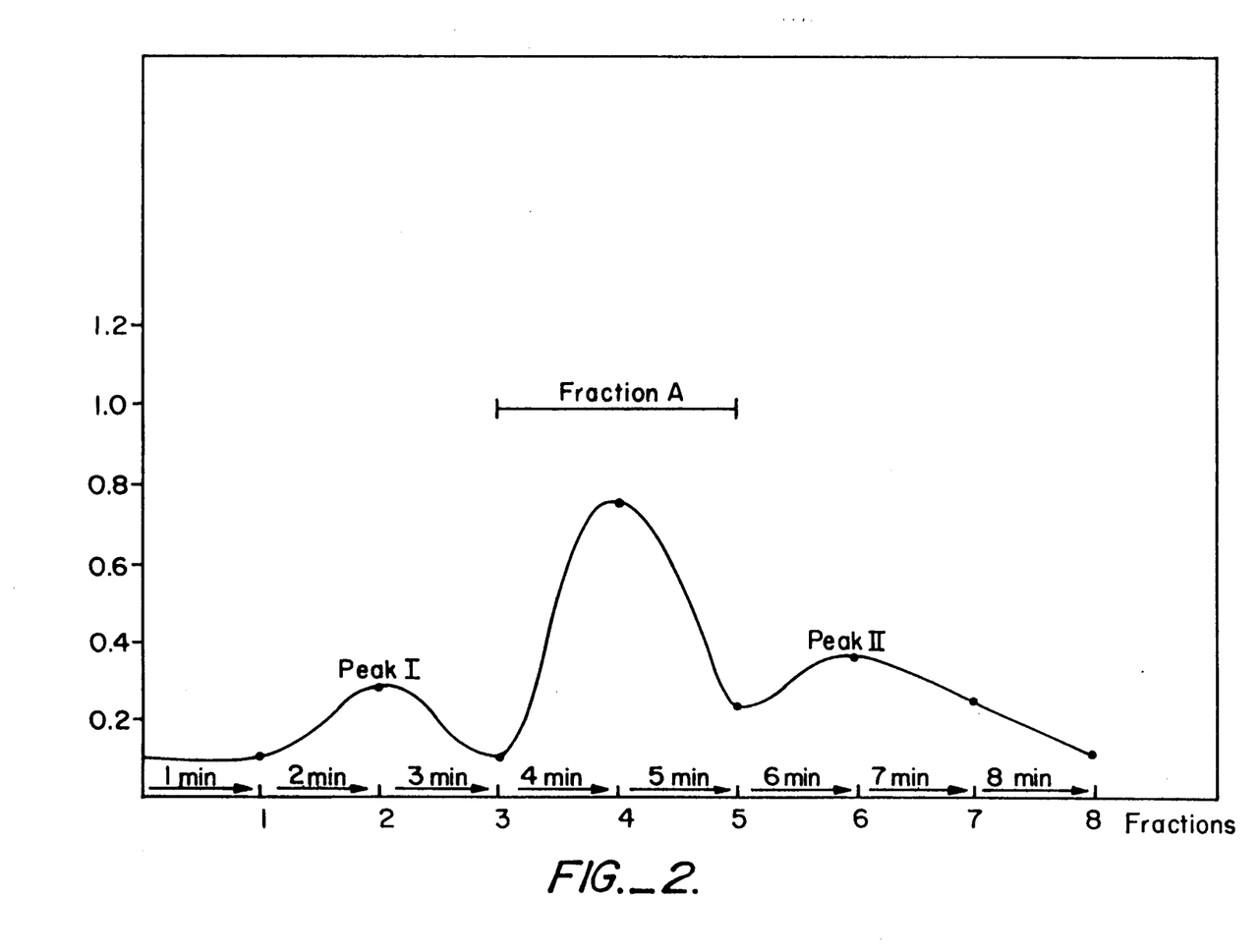
FIG. 2 shows an elution profile at 270 nm of the separation of Cp riboflavin from unreacted riboflavin and cytidine 2',3'-cyclic phosphate using an intermediate pressure chromatography column run at 1.05 kg/cm² nitrogen with $H_2O$:pyridine:acetic acid.

An aliquot of the phenol and chloroform extracted incubate from stage II (10 ml) was applied to a column of silica gel (Merck silica gel 60) and eluted in H$_2$O, 40: pyridine, 10: glacial acetic acid, 1, under a positive pressure of oxygen free nitrogen 15 lbs/in$^2$ (1.05 kg/cm$^2$). (FIG. 2)

Figure 3:
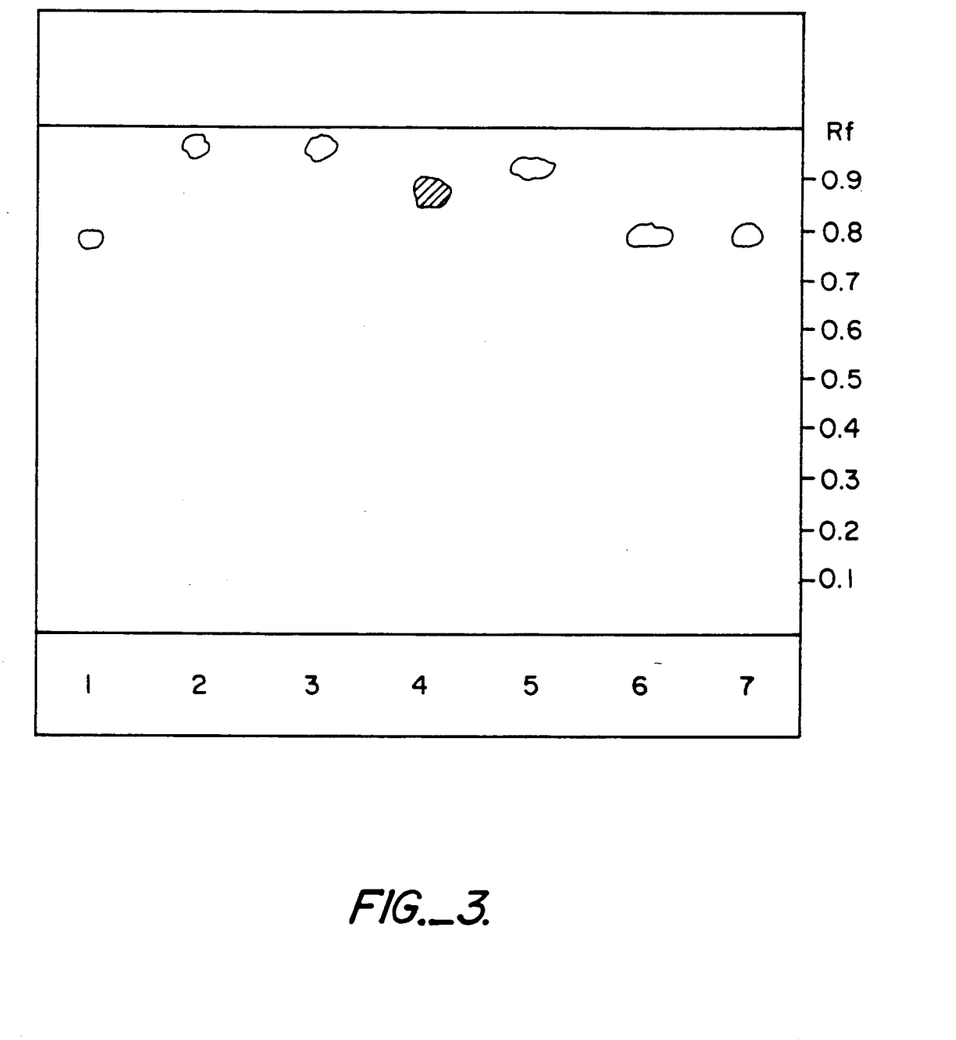
FIG. 3 shows a thin layer chromatogram of the pooled elution products, the lanes on the gel being as follows:
1. Riboflavin (5 ug).
2. Peak I (flash chromatography).
3. Cytidine 2',3'-cyclic phosphate (5 ug).
4. Fraction A (flash chromatography).
5. CpA (5 ug).
6. Peak II (flash chromatography).
7. Riboflavin (5 ug).

Fractions were pooled and assayed by thin layer chromatography as described previously. (FIG. 3)

Figure 4:
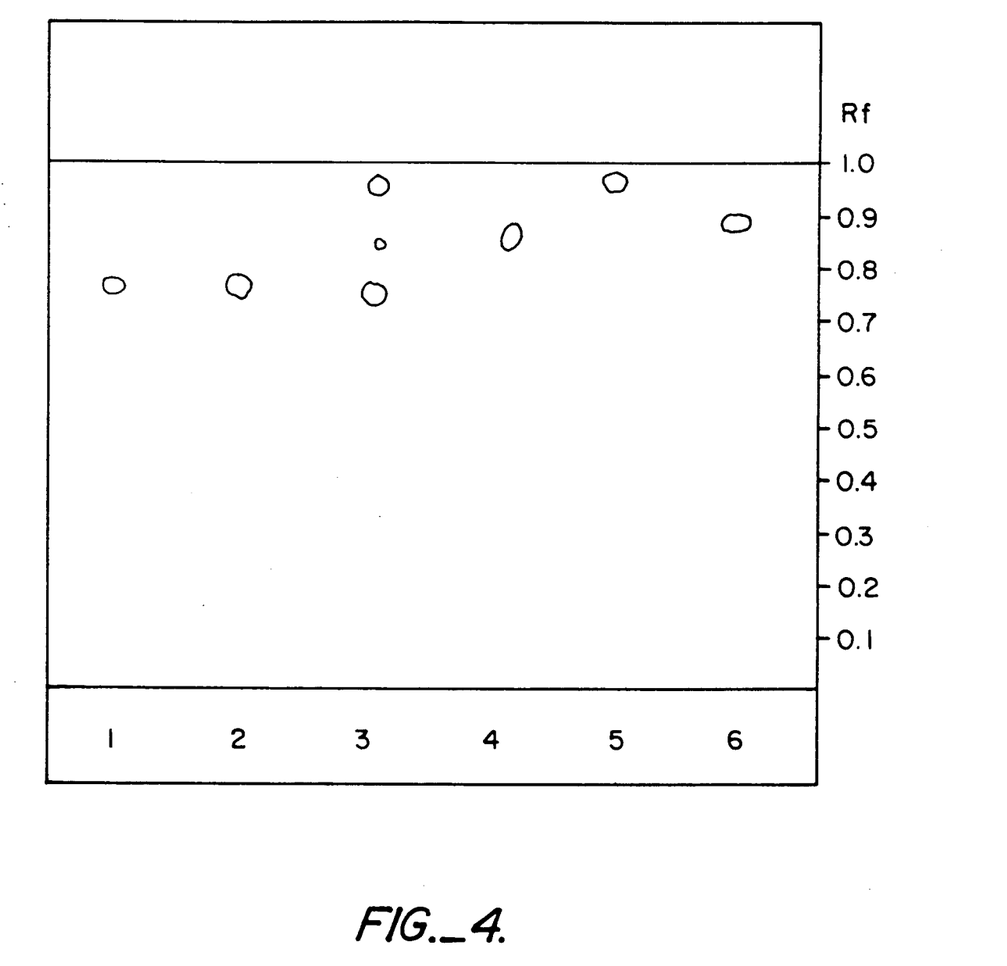
FIG. 4 shows a thin layer chromatogram of column fraction A after incubation with RNAse (1 mg/ml), the lanes on the gel being as follows:
1. Riboflavin ($1.3 \times 10^{-4}$M)+1 mg/ml RNAse A.
2. Riboflavin (5 ug).
3. Evaporated column fraction A+1 mg/ml RNAse.
4. Evaporated column fraction A: No RNAse.
5. Cytidine 2',3'-cyclic phosphate.
6. CpA.

Fraction A (FIG. 2 and track 4 FIG. 3) was tested as a substrate for ribonuclease by incubating an aliquot (100 μl) in a mixture containing 2 mg of ribonuclease in a final volume of 1 ml of 0.1M ethylene diamine buffer pH 6.50 for 2 hours at room temperature. The resultant chromatogram showed that the spot at Rf 0.87 was resolved into 2 spots of Rf 0.79 (riboflavin) and 0.96 (cytidine 3'-phosphate), indicating that the product was hydrolysed by RNase into its constituent components. (FIG. 4)

Fraction A (FIG. 2) was pooled and rotary evaporated at 55° C. to obtain a solid. However, a residual volume of formamide remained which was not removed during the phenol extraction protocol and which moved with the mobile phase during intermediate pressure chromatography. Removal of the formamide provides the substrate in solid form.

Primary Reactions

The desired active form of the coenzyme, FMN, is generated by the action of riboflavin kinase (flavokinase: EC 2.7.1.26) an enzyme that is readily prepared.

There are many candidates for the detecting enzyme employing FMN as the coenzyme, including glycolate oxidase [EC 1.1.3.1 Schuman & Massey (1971)] from which FMN can be removed by dialysis against 1M KBr [Massey & Curti (1966)]; L-hydroxyacid oxidase [EC 1.1.3.15, Nakano et al (1968)] and orotate reductase from Zoroticum [EC 1.3.1.14, Swell et al (1960)], but a particularly preferred one is pneumococcal L-lactate oxidase [EC 1.13.12.4, Udaka et al (1959)].

This enzyme catalyses reaction (i):

$$\text{Lactate} + O_2 \rightarrow \text{acetate} + CO_2 + H_2O \quad \text{(i)}$$

which is inconvenient for assay purposes. However in the presence of catalase the reaction becomes [Udaka et al (1959)]:

$$\text{Lactate} + \tfrac{1}{2}O_2 \rightarrow \text{pyruvate} + H_2O \quad \text{(ii)}$$

Thus the enzymic reaction is:

$$\text{Lactate} + O_2 \rightarrow \text{pyruvate} + H_2O_2 \quad \text{(iii)}$$

This presents the opportunity of coupling the reaction to one of the rapid and sensitive methods for detecting H$_2$O$_2$, such as the reaction with the chromogenic substrates, 5-aminosalicyclic acid or dianisidine, catalysed by horseradish peroxidase [Kas & Cerna (1980)].

An alternative is to couple the production of FMN to the generation of flavodoxin. Apoflavodoxin is a well-documented detector for FMN or FAD in a system in which the extent of the change in fluorescence of the flavin nucleotide on combination with the apoprotein is used to determine the amount of the nucleotide in an unknown solution [Mayhew & Wassink (1980): a & b]. However the fluorescence method would be insufficiently sensitive for the present purposes, so an enzyme-linked assay can be used e.g. the flavodoxin-mediated reduction of cytochrome c by NADPH catalysed by the purified reductase [Shin (1971)].

Although FMN-coupled enzymes are proposed for the coenzyme coupling assays described above, the range of enzymes that could be employed can be expanded to those using FAD as coenzyme. This would involve the extra reaction catalysed by FMN adenyl-transferase: [Gibson et al (1955) and Schrecker & Kornberg (1950)]

$$\text{FMN} + \text{ATP} \rightleftharpoons \text{FAD} + \text{PP} \quad \text{(iv)}$$

where the FMN would have arisen from the flavokinase reaction.

This would enable, for example, D-amino acid oxidase to be employed as a coupling enzyme. The apoenzyme from this oxidase is prepared readily by the KBr dialysis method [Massey & Curti (1966)] and is stable for at least several months if stored at −20° C. The assay of D-amino acid oxidase by coupling with a peroxidase-catalysed reaction is well-documented and offers the opportunity of a chromogenic visualisation of the enzyme [Tsuge & Nakanishi (1980)].

Other FAD enzymes could be employed in similar fashion including glucose oxidase; L-amino acid oxidase and xanthine oxidase [Tsuge & Nakanishi (1980)]. It remains to be established which system would be the most favourable but each of these enzymes is readily available and can be treated to give stable apoenzymes.

The detection system using pyridoxal phosphate as the coupling coenzyme Aspartate aminotransferase (EC 2.6.1.1) catalyses the reaction of α-oxoglutarate (αOG) with (S)-aspartate (Asp) to form oxaloacetic acid (OAA) and (S)-glutamate (Glu). The enzyme contyains pyridoxal phosphate as a coenzyme and the holo enzyme can be readily and reversibly resolved into free coenzyme and apoenzyme [Martinez-Carrion et al 1970]. A sensitive assay for the holoenzyme (nanomolar concentrations) has been described by Raj (1982) based on the formation of a coloured reduced neotetrazolium derivative INT* red coupled to the reaction catalysed by glutamate dehydrogenase.

A procedure for probe-S-peptide detection using asparate aminotransferase as Holo 1 is as follows:

Compound IV can be synthesised by a procedure similar to that published for Cp benzyl [Bernard & Witzel 1961]. Pyridoxal, shown as the hydrate, formed by the above reaction, is converted to the pyridoxal phosphate required in the reaction catalysed by pyridoxal kinase (EC 2.7.1.35).

where $S_1C_1$ is a cytidine 3'-phosphodiester with pyridoxal (Py), pyridoxamine or pyridoxal as the $C_1$ moiety.

A possible substrate ($S_1C_1$) for RNase action giving pyridoxal as one of the products is compound IV which is hydrolysed as follows:

Other possible substrates include compounds V–VII:

where Cp represents cytidine 3'-phosphoryl- and R is either H- or -O-P(OH)$_2$.

Compound V on hydrolysis by RNase S would give pyridoxol, which is converted to pyridoxal using pyridoxol oxidase (EC 1.4.3.5) in the assay system as an additional step before the kinase-catalysed reaction. If compound VI, the phosphorylated form of compound V, is used as a substrate for RNase S, pyridoxal phosphate would be generated directly by the action of the oxidase. Compound VII, in which the cytidine 3'-phosphoryl group is in a phosphodiester link at the phenolic oxygen of pyridoxal, under RNase-catalysed hydrolysis would likewise give pyridoxal phosphate directly. However it is known that the enzymic specificity is such that bulky substituents on the oxygen atom of the leaving group are poorly tolerated so this substrate may be less preferred.

Compounds V and VI can be prepared enzymically by using RNase to catalyse the condensation reaction in formamide/water or other aprotic solvent/water mixtures [Findlay, Mathias & Rabin (1962)]. Chemical synthesis using a phosphotriester-based approach with suitably protected reactants may be employed to synthesise compound VII as well as compounds V and VI.

A preparation of the apoenzyme apo glutamic-aspartic transaminase (Apo 1) has been described [Martinez-Carrion (1970), Arrio-Dupont M. (1972)] and is best carried out in stages: first replacing the pyridoxal-phosphate with the less affine pyridoxamine phosphate and then removing the latter by using gel chromatography. The apoenzyme is stable for long periods. Removal of all the pyridoxal phosphate is essential for good signal-to-noise ratio but this is ensured by an inhibition step involving treatment with a ketoacid and then NaBH$_4$, which inactivates any residual enzymic activity in the preparation of the apoenzyme.

Reconstitution of Holotransaminase from pyridoxal phosphate and the apoenzyme has been described in an elegant paper by M. Arrio-Dupont (1972). Typically, a concentration of apotransaminase of 0.1 $\mu$M or greater is employed. This concentration is sufficient to ensure essentially stoichiometric conversion to holotransaminase of any low concentration of pyridoxal phosphate formed in the system.

A DOUBLE AMPLIFICATION SYSTEM USING DOUBLE COENZYME COUPLING

It is clear that in principle "cascades" can be built up to make the assay systems as sensitive as required.

A potentially very sensitive system is described below. The double amplification arises from the primary catalyst releasing a coenzyme (eventually FAD) which combines with an apooxidase to generate a second coenzyme, pyridoxal phosphate, which in turn activates the second apoenzyme.

PROBE-ENZYME CLEAVAGE

As indicated above, one aspect of the procedure of the invention lies in the possibility of removing the primary enzyme ($E_o$ in scheme 1) from the detection system prior to carrying out the primary enzymic reaction. This has the advantage that the primary reactions, sensitivity enhancement and detection can be carried out in free solution away from the polynucleotide analyte and oligonucleotide probe. This cleavage of the probe-enzyme fraction bond can be effected prior to conjugating the larger enzyme fraction to complete the enzyme, or after conjugation but before adding the substrate. By way of example: if the analyte is a polynucleotide, the probe is an oligonucleotide hybridisable therewith, and the smaller enzyme fraction is S-peptide linked to the oligonucleotide through a disulphide bond; this bond can be cleaved using conventional reducing agents such as dithiothreitol or $\beta$-mercaptoethanol to release the S-peptide once more. Thus, Spep-probe can be added to the sample, and unbound Spep-probe removed by washing. Then the S-peptide is cleaved from the probe and reacted with excess S-protein to form the enzyme conjugate; or else the S-protein can be added to the Spep-probe followed by cleavage of the conjugate from the probe. A specific example could involve: (i) immobilising the analyte on a support, such as a polymeric or absorbent solid; (ii) reacting the immobilised analyte with excess Spep-probe in solution; (iii) removing the support with its bound analyte-Spep-probe complex from the solution, and washing to remove any unbound Spep-probe; (iv) immersing the support in a solution of a cleaving agent which cleaves the Spep from the support so that it goes into solution; (v) adding S-protein to the solution to form the enzyme conjugate, and carrying out the enzymic reactions to produce the detectable result. Step (v) could involve the single addition to the solution of all the other reagents, along with the S-protein, to complete the assay reactions. As an alternative, the S-peptide could be initially immobilised on a support, so that the subsequent cleavage step removes the analyte and probe, leaving the S-protein to conjugate with the S-peptide on the support. In this way the primary enzymic reaction, and possibly the subsequent reactions, can take place on the support, which could be easier and more sensitive for identifying the detectable result of the reactions.

The separation of the primary enzyme from the probe prior to carrying out the primary enzyme catalysed reaction could be advantageous in that the probe and analyte will then not interfere with the activity of the enzyme. Likewise, cleaving the small enzyme fraction (Spep) from the probe before conjugating it with the larger fraction (Spr) avoids the probe or analyte interfering with the conjugation.

Prosthetogens

The concept of synthetic prosthetogens can be applied more generally than in the specific examples illustrated above. For instance, ribonuclease (RNase) can be used as a primary enzyme linked indirectly to the probe such as by a biotin-avidin linkage as described in GB 2019408. The RNase can then act on the novel synthetic prosthetogen R-X substrate described above to give a coenzyme precursor, leading ultimately to a detectable result via the secondary enzymic reaction.

Moreover, the primary enzyme for the prosthetogen reaction need not be RNase. Starting with a suitable coenzyme or prosthetic group for the secondary reaction, a reaction scheme is formulated having as a primary reaction the enzymically catalyzed cleavage of a synthetic starting material (the novel prosthetogen). For example the prosthetogen may be an acylated coenzyme and the primary enzyme an esterase which cleaves the acyl group from the coenzyme. If the esterase is cleavable into inactive peptide and protein fragments, it can be used as described earlier for RNase Spep/Spr. If it is not cleavable in that manner, it can be linked as a whole to the probe, e.g. directly, or by biotin/avidin, but preferably by RNase Spep/Spr. In this latter procedure, Spep is linked to the probe as described earlier, and Spr is linked to the enzyme. General methods for joining proteins are well known in the art, and can be used for linking the Spr fragment with the enzyme. This procedure, in which S-protein acts as a carrier for other enzymes can be represented as follows:

-continued

Key
Spr - Ex: S-protein containing a covalently bound enzyme molecule, Ex. Other species are as described earlier.

The following description is of procedures that employ pyridoxal phosphate and flavin coenzymes but any appropriate cofactor could be used to generate other detection systems.

Systems with pyridoxal as the coupling coenzyme

With this procedure the final detection system would be identical to that described earlier. The primary catalyst, attached to the S-protein could be any of a wide selection of hydrolytic enzymes, such as proteases, peptidases, amidases or esterases, and especially thrombin or one of the other specific proteases of the blood-clotting system. With thrombin as the primary catalyst (Ex), the synthetic prosthetogen coenzyme-generating substrate $S_1C_1$ could be compounds such as VIII-X where $R_2$ is either H- or $-PO.(OH)_2$ and $R_1$ is an acyl group designed in the light of the known specificity of thrombin to make the compound a good substrate for thrombin action (Magnusson (1971) and references therein). Hydrolysis of VIII gives pyridoxamine (phosphate), and IX and X both release pyridoxal or pyridoxal phosphate. If the aldehyde (hydrate) group in IX and X is replaced with a $-CH_2OH$ group and the coupling effected through pyridoxol oxidase, it should prove less inhibitory and less prone to oxidation.

Compounds VIII-X can be synthesized from $R_1COOH$ and the pyridoxal derivative by straightforward methods such as those described by Harrison & Harrison (1971). Preparation of suitable $R_1COOH$ derivatives would be as described by Liem & Scheraga (1974).

Structures of coenzyme-generating substrates for cholinesterase and compounds XI and XII:

where R = H or $-\underset{\underset{O}{\|}}{P}(OH)_2$

Substrates XI and XII can be synthesized by using one of the usual methods for esterification (Harrison & Harrison (1971)) following protection of the appropriate groups in pyroxidal. To avoid any reaction of the aldehyde group of pyridoxal (shown above as the hydrate) with a group in the active site of cholinesterase, pyridoxol can be the leaving group and pyridoxol oxidase and the kinase used as modifying enzymes as described earlier.

Systems with flavin derivatives as the coupling coenzymes

Such systems would use the end-detectors for flavin-coupled assays described earlier and the primary catalysts described in the previous section. The types of substrates ($S_1C_1$) that would be employed would have structure XIV for the thrombin action and XV for the case where cholinesterase is the primary catalyst:

XIV, $R_1$ = peptide fragment
XV, $R_1$ = $CH_3$

Chemical syntheses of the esters XIV and XV are by one of the methods described by Harrison & Harrison (1971); for example carbodiimide-mediated esterification of flavin with the carboxylic acid $R_1COOH$, with purification of the substrate by HPLC.

REFERENCES

Arrio-Dupont, M. (1972) European J. Biochem. 30, 307.
Barnard, E. A. & Witzel, H. (1962) Biochem. Biophys. Res. Commun. 7, 289.
Brown, D. M. & Todd, A. R. (1953) J. Chem. Soc. 2040.
Chavers, L. G. & Scheraga, H. A. (1980) Biochemistry 19, 996.
Cheng, S. -Y., Clenn, T. M. and Pastan, I. (1983) Nucl. Acids Res. 11, 659.
Choong, Y. S., Shepherd, M. G. & Sullivan, P. A. (1975) Biochem. J. 145, 37.
Doscher, M. S. (1969) Methods in Enzymology 11, 640.
Findlay et al. 1962—see elsewhere.
Froede, H. C. & Wilson, I. B. (1971) in "The Enzymes", 3rd Ed. ed Boyer V 87.
Fujikawa, K. & Davie, E. W. (1976) Methods in Enzymol. XLV, 89.
Gait, M. J., Matthes, H. W. D., Singh, M., Sproat, B. & Titmas, R. C. in EMBO Course Manual (1982) Publ. Verlag Chemie.
Ghisla, S., Ogata, H., Massey, V., Schonbrunn, A., Abeles, R. H. & Walsh, C. T. (1976) Biochemistry 15, 1791.
Gibson, K. D., Neuberger, A. & Scott, J. J. (1955) Biochem. J. 61, 618.
Harrison, I. T. & Harrison, S. H. (1971) in "Compendium of Organic Synthetic Methods" pp. 280-286 and 204-207 and 213-218.
Itakura, K., Katagiri, N., Narang, S. A., Bahl, C. P., Marians, K. J. & Wu, R. (1975) J. Biol. Chem. 250, 4592.
Itakura, K., Katagiri, N., Bahl, C. P., Wightman, R. H. & Narang, S. A. (1975) J. Am. Chem. Soc. 97, 7327.
Jesty, J. & Nemerson, Y. (1976) Methods in Enzymol. XLV, 95.
Kas, J. & Cerna Jitka (1980) Methods in Enzymol. 66, 344.
Liem, R. K. H. & Scheraga, H. A. (1974) Archives Biochem. Biophys. 160, 333.
Magnusson, S. (1971) in "The Enzymes" III (rd ed) ed. Boyer, P. D. p. 278.
Marfrey, P. S., Nowak, H., Uziel, M. & Yphantis, D. A. (1965) J. Biol. Chem. 240, 3264 & 3270.
Martinez-Carrion, M., Tiemeier, D. C. & Peterson, D. (1970) Biochemistry 9, 2574.
Massey, V. & Curti, B. (1966) J. Biol. Chem. 241, 3417.
Mayhew, S. G. & Wassink, J. H. (1980) Methods in Enzymol. 66, 217.
Mayhew, S. G. & Wassink, J. H. (1980) Methods in Enzymol. 66, 323.
McCormick, D. B. (1962) J. Biol. Chem. 237, 959.
Merrill, A. H. & McCormick, D. B. (1978) Anal. Biochem. 89, 87.
Merrill, A. H. & McCormick, D. B. (1980) Methods in Enzymol. 66, 287.
Nakano, M., Ushijima, Y., Saga, M., Tsutsumi, Y. & Asami, H. (1968) Biochim. Biophys. Acta 167, 9.
Rej. R. (1982) Anal. Biochem. 119, 205.
Richards, F. M. & Vithayathil, P. J. (1959a) J. Biol. Chem. 234, 1459.
Richards, F. M. & Vithayathil, P. J. (1959b) Brookhaven Symp. in Biol. 13, 115.
Roychoudhury, R., Jay, E. & Wu, R. (1976) Nucl. Acids Res. 3, 863.
Schoellman, G. & Shaw, E. (1962) Biochem. Biophys. Res. Commun. 7, 36.
Schrecker, A. W. & Scott, J. J. (1955) Biochem. J. 61, 618.
Schuman, M. & Massey, V. (1971) Biochim. Biophys. Acta 227, 500.
Shin, M. (1971) Methods in Enzymol. 23A, 440.
Stawinkski, J., Hozumi, Y., Narang, S. A., Bahl, C. P. & Wu, R. (1977) Nucleic Acids Res. 4, 353.
Swell, L., Law, M. D., Field, H. & Treadwell, C. R. (1960) Biochim. Biophys. Acta 235.
Takahashi, T., Irie, M. & Ukita, T. (1969) J. Biochem. (Tokyo) 65, 55.
Todrick, A. (1954) Brit. J. Pharmacol. 9, 76.
Tsuge, H. & Nakanishi, Y. (1980) Methods in Enzymol. 66, 344.
Udaka, S., Koukol, J. & Vennesland, B. (1959) J. Bacteriol. 78, 714.
Ward, D. C., Waldrop, A. A. III, Langer, P. A., (1982) EP 63879.
Wightman, R. H. & Narang, S. A. (1975) Nucleic Acids Res. 4, 353.
Eckstein, F., Saenger, W. & Suck, D. (1972) Biochem. Biophys. Res. Comm. 46, No. 2, 964-971.
Still, W. C., Kahn, M. & Mitra, A. (1978) J. Org. Chem. 43, No. 14, 2923-2925.
Usher, D. A., Erenrich, E. S. & Eckstein, F. (1972) Proc. Nat. Acad. Sci. U.S.A. 69, No. 1, 115-118.

We claim:
1. An enzyme linked assay procedure in which a primary enzyme whose concentration is related to the presence of analyte to be detected catalyses a primary enzymic reaction leading to a detectable product, said assay procedure comprising the steps of
   i. using as said primary enzyme a phosphodiesterase and contacting the primary enzyme with a substrate therefor comprising a pyrimidine ribonucleoside 3'-phosphodiester compound of the formula R—X, where R is a pyrimidine ribonucleoside 3'-phosphate and X is a leaving group linked to R through a 3'-phosphate group, so that said X is cleaved away by the primary enzyme to produce directly, or by one or more further reactions, a coenzyme or prosthetic group essential for the catalytic activity of another enzyme, and
   ii. using the coenzyme or prosthetic group to activate said other enzyme to catalyze a secondary enzymic reaction leading to a detectable result related to the presence of analyte.

2. An assay procedure according to claim 1 wherein a prosthetic group is produced in step (i) and is an enzymically inactive first component of said other enzyme which in step (ii) combines with an enzymically inactive second component of said other enzyme, whereby said other enzyme is activated to catalyze a secondary enzymic reaction leading to a detectable result.

3. An assay procedure according to claim 1 wherein a coenzyme is produced in step (i) and is used in step (ii) to activate said other enzyme.

4. An assay procedure according to claim 1 wherein the primary enzyme is a ribonuclease.

5. A combination for carrying out the procedure of claim 1, the combination comprising:
   (i) said substrate for said primary enzyme,
   (ii) components for the other enzyme reaction to be activated by the product of the primary enzymatic reaction, and
   (iii) a signal producing system activatable by said other enzymic reaction to produce a detectable result.

6. An assay procedure according to claim 1 wherein the leaving group product is selected from the group consisting of riboflavin, thiamine, pyroxidal, pyridoxine and pyridoxine phosphate.

7. An assay procedure according to claim 6 wherein said leaving group product is converted to a coenzyme or prosthetic group for said other enzyme selected from the group consisting of flavin mononucleotide, flavin adenine dinucleotide, thiamine diphosphate and pyridoxal 5-phosphate.

8. An enzyme-linked assay procedure in which a primary enzyme whose concentration is related to the presence of an analyte to be detected catalyses a primary enzymic reaction leading to a detectable product, said assay procedure comprising the steps of
   i. contacting the primary enzyme with a synthetic, non-naturally occurring, prosthetogen compound which is thereby cleaved by the primary enzyme, to produce directly, or by one or more further reactions, a non-substrate coenzyme or prosthetic group which binds to, and is essential for the catalytic activity of, another enzyme, and
   ii. using said coenzyme or prosthetic group to activate said other enzyme so as to catalyse a secondary enzymic reaction leading to a detectable result related to the presence of analyte.

9. An enzyme-linked assay procedure in which a primary enzyme whose concentration is related to the presence of analyte to be detected catalyses a primary enzymic reaction leading to a detectable product, said assay procedure comprising the steps of
   i. contacting the primary enzyme with a synthetic, non-naturally occurring, prosthetogen compound which is thereby cleaved by the primary enzyme to produce directly, or by one or more further reactions, a riboflavin-containing prosthetic compound essential for the catalytic activity of another enzyme, and
   ii. using the prosthetic compound to activate said other enzyme so as to catalyse the secondary enzymic reaction leading to a detectable result related to the presence of analyte.

* * * * *